United States Patent [19]

Shiraiwa et al.

[11] 4,294,118

[45] Oct. 13, 1981

[54] FULLY AUTOMATIC ULTRASONIC FLAW DETECTION APPARATUS

[75] Inventors: Toshio Shiraiwa; Hisao Yamaguchi; Shigeaki Matsumoto, all of Amagasaki, Japan

[73] Assignee: Sumitomo Kinzoku Kogyo Kabushiki Kaisha, Osaka, Japan

[21] Appl. No.: 89,277

[22] Filed: Oct. 29, 1979

[51] Int. Cl.³ ............................................ G01N 29/04
[52] U.S. Cl. ..................................................... 73/620
[58] Field of Search ................. 73/620, 621, 627, 629, 73/632, 633, 634

[56] References Cited

U.S. PATENT DOCUMENTS 3,575,042  4/1971  Lovelace et al. ...................... 73/620
4,041,379  8/1977  Karlsson ................................ 73/620
4,170,145  10/1979  Kennedy et al. ..................... 73/620
4,213,183  7/1980  Barron et al. .......................... 73/634

Primary Examiner—Stephen A. Kreitman

Attorney, Agent, or Firm—Wenderoth, Lind & Ponack

[57] ABSTRACT

Disclosed herein is a fully automatic ultrasonic flaw detection apparatus convenient for flaw detection in a weld zone such as found in an welded iron structure. The apparatus includes a scanner for moving a ultrasonic transmitting and receiving probe in directions parallel to and perpendicular to the longitudinal direction of the object to be inspected or the testpiece, and an information processing unit for controlling the action of the scanner and processing received reflected ultrasonic wave flaw detection data. The probe is alternately moved parallel to and perpendicular to the longitudinal direction of the testpiece according to a predetermined scanning routine to perform rough flaw detection and the results of this rough flaw detection are produced as output. When the presence of flaw is detected during this rough flaw detection routine, the probe is returned to a position necessary to perform precision flaw detection of that flaw.

8 Claims, 16 Drawing Figures

FULLY AUTOMATIC ULTRASONIC FLAW DETECTION APPARATUS

BACKGROUND OF THE INVENTION

This invention relates to a ultrasonic flaw detection apparatus for fully automatic ultrasonic flaw detection by use of an information processing unit, which has gained wide application as one non-destructive test technique for the weld zone of a steel product. More specifically, the present invention is an ultrasonic flaw detection apparatus which first performs preliminary flaw detection for the range required and then performs flaw detection at the position of a flaw if such a flaw is present within the range.

Flaw detection of the weld zone of a steel product is generally carried out by, for example, arranging one or more probes on both sides of the weld zone and moving the probe or probes once in a direction parallel to the longitudinal direction of the weld zone. However, this method involves a problem because flaws in the weld zone or in portions near the weld bond can not always be detected in the most desirable state and hence, the flaw detection tends to be inaccurate. A more advanced method, the so-called "precision flaw detection method" is also practised at present. In this method the above-mentioned preliminary flaw detection is carried out once, and then the probe or probes are returned by manipulation of the probe-scanning mechanism to the position of the weld zone where the flow is judged present, in order to again evaluate the flaw. However, this manipulation of the scanning mechanism must be made manually and is therefore troublesome and time-consuming.

Especially for flaw detection of the weld zone between mating steel bars of a high-storied structure, manipulation of the probe-scanning mechanism becomes very complicated and difficult due to the limited working space, thereby causing various practical difficulties and reducing work safety.

SUMMARY OF THE INVENTION

The present invention is proposed to solve the above-mentioned problems.

It is therefore a first object of the present invention to provide a ultrasonic flaw detection apparatus which performs automatic flaw detection of a test object such as the weld zone and nearby portions, to automatically process flaw detection data, to automatically return the probe to the required scan position to evaluate again the flaw when the presence of such a flaw is detected and to produce, as an output, the flaw detection results of a series of flaw detection operations for the purpose of recording and displaying these results, thereby improving the flaw detection accuracy, simplifying the flaw detection work and shortening the time required for flaw detection.

It is a second object of the present invention to provide an ultrasonic flaw detection apparatus which automatically scans in a direction parallel to the longitudinal direction of the test object and then automatically scans in another direction perpendicular to the first direction alternately with each other in order to simplify the scanning mechanism and to easily recognize the scanning position and hence, the position of flaw detection.

It is a third object of the present invention to provide an ultrasonic flaw detection apparatus wherein the probe rides over the weld zone from one side to the other when flaw detection on one side of the weld zone is completed and carrying out subsequent flaw detection on the other side. Though only one probe is used, the apparatus performs precision flaw detection from both sides of the test object once the apparatus is started.

It is a fourth object of the present invention to provide an ultrasonic flaw detection apparatus wherein the probe is constructed to cause oscillation on the face of the test object which the probe contacts, in order to detect the flaw or flaws not following in the same direction as that of the linear test object from the best direction and thus achieve flaw detection with a high level of accuracy.

BRIEF DESCRIPTION OF THE DRAWINGS

Other objects, features and advantages of the present invention will be apparent from the following detailed description taken in conjunction with the accompanying drawings, in which.

DETAILED DESCRIPTION OF THE INVENTION

Figure 2:
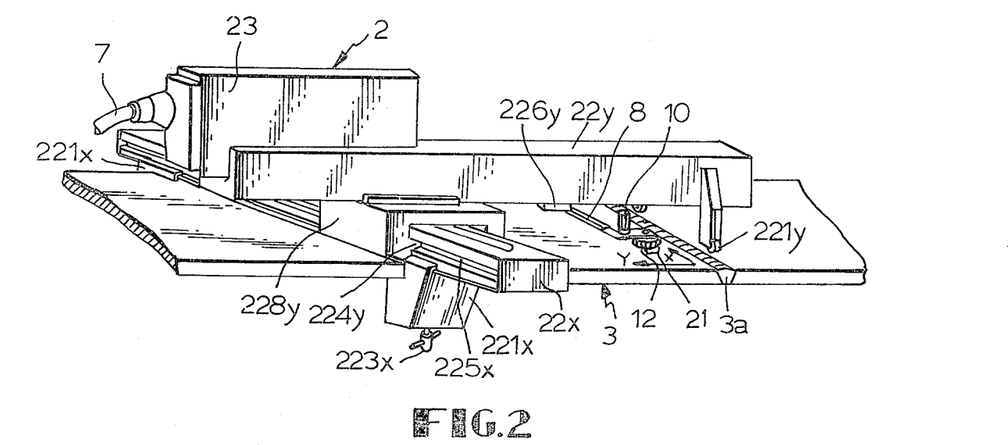
FIG. 2 is a perspective view of the scanner.

Initially, an explanation will be made of the apparatus of the present invention as a whole. The apparatus of this invention broadly consists of a flaw detection mechanism such as a scanner 2 which is fitted to a testpiece 3 such as the steel skeletal weld zone of sheet steel or shaped steel which moves an ultrasonic wave probe 1b in two directions at right angles to each other along the surface of the testpiece 3, and a signal processing unit which generates an ultrasonic wave in the probe 1b, analyzes the ultrasonic wave signal picked up by the probe and controls the action of the scanner. As shown in FIG. 2, the scanner 2 is fitted to the testpiece 3 having a weld zone 3a extending in the transverse direction in such a manner that the direction of motion of the probe 1b for flaw detection scanning is perpendicular to the longitudinal direction of the weld zone 3a (hereinafter referred to as the "X-axis direction") and also to its transverse direction (hereinafter referred to as the "Y- axis direction"). The flaw scanning mechanism is electrically connected to the signal processing unit 1, which is independent of the scanning mechanism, via a cable 7 inserted into the rear surface of motor case 23 which incorporates two pulse motors 23x and 23y therein.

Figure 1:
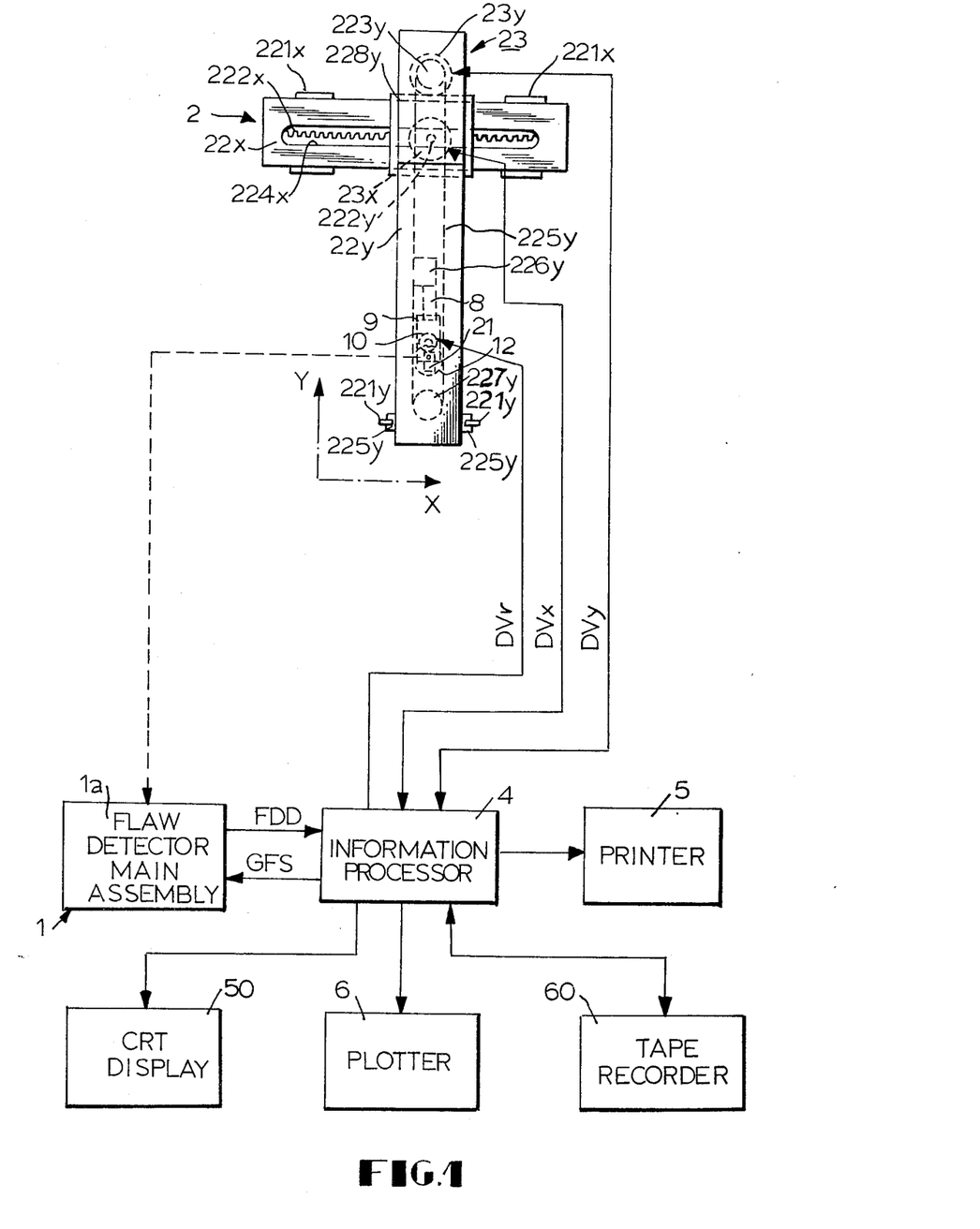
FIG. 1 shows a block diagram of the signal processing system of the apparatus according to the present invention and a plan view of its scanner.

The probe 1b of the flaw scanning mechanism together with the flaw detector main assembly 1a of the signal processing unit constitutes an ultrasonic flaw detector. It receives intermittent high frequency signals from the detector 1a for transmitting the ultrasonic waves and when reflected waves from the flaw, etc. are present, makes an acousto-electric conversion of the reflected waves and returns them to the ultrasonic detector 1a. An information processing unit 4 (hereinafter referred to as the "computer") forms the center of the signal processing unit as shown in FIG. 1, and generates drive signals to the pulse motors 23x and 23y which move the probe 1b in the X-axis direction and in the Y-axis direction, respectively. Computer 4 also generates a drive signal to motor 10 for turning the probe 1b by 180 degrees. The computer 4 is interconnected with the detector 1a in order to process the detection signals received by the latter.

Figure 3:
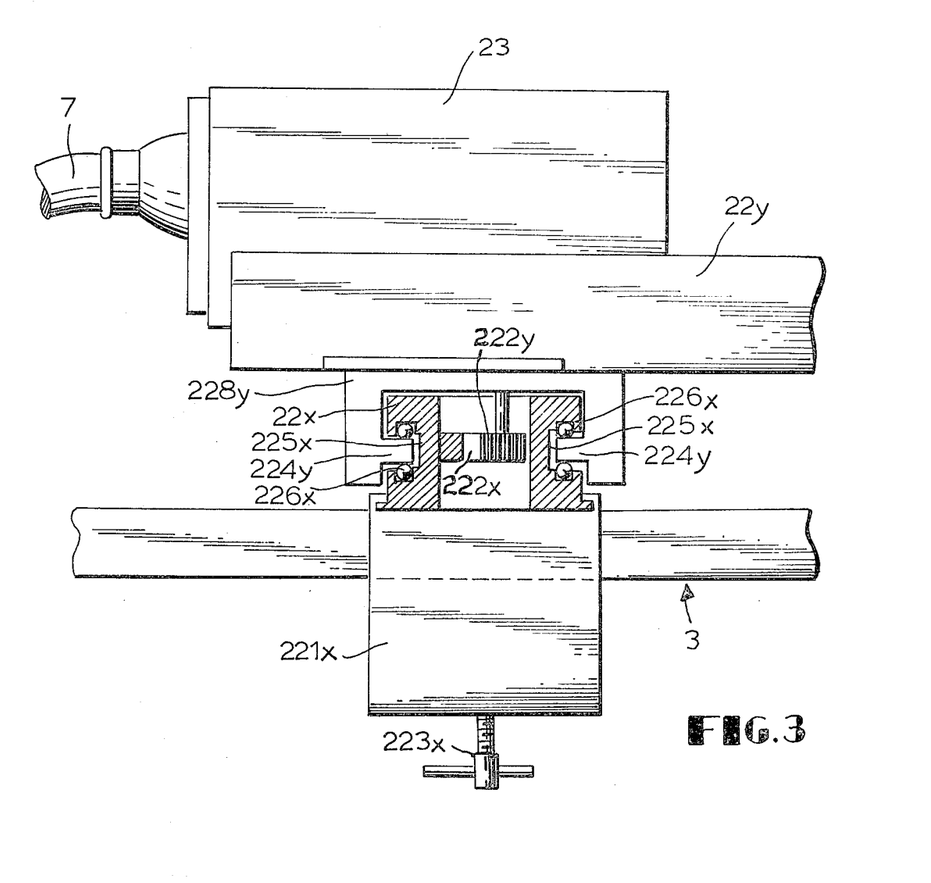
FIG. 3 is a sectional side view showing the engaging structure between the guide frame in the X direction and the guide frame in the Y direction of the scanner.

Explanation will next be made of the construction of the flaw detection mechanism in further detail. Reference numeral 22x represents a guide frame which is fitted to the testpiece 3 parallel to the X-axis direction and which is secured thereto by clamp screws 223x which screw into two legs 221x (though only one is shown in FIG. 2) formed near each end of guide frame 22x in its longitudinal direction. An elongated groove 224x is formed in the upper face of the guide frame 22x extending in the longitudinal direction. A rack 222x having substantially the same length as the elongated groove 224x is placed inside the elongated groove 224x. Rack 222x has teeth directed toward the front of the apparatus (in the direction of probe 1b) defining a suitable gap between the teeth of rack 222x and the elongated groove 224x. As shown in FIG. 3, recessed grooves 225x are formed in the front and rear surfaces of guide frame 22x extending over its entire length and a linear bearing 226x is fitted into each recessed groove 225x opposite each other on the upper and lower faces extending over the entire length of each groove.

A guide frame 22y equipped with the probe 1b and with the motor case 23 is mounted onto the guide frame 22x crossing the guide frame 22x at a right angle, that is to say, extending in the Y-axis direction. Reference numeral 228y represents a slide leg of the guide frame 22y which has a gate shape as shown in FIG. 3. Protuberances 224y are formed on the inner faces of the opposed walls of the front and rear faces of the slide leg so as to engage with the aforementioned recessed grooves 225x thus joinng the guide frame 22y with the guide frame 22x. The guide frame 22y is allowed smooth motion in the X-axis direction with respect to the guide frame 22x by the action of the linear bearings 226x.

On the other hand, wheel legs 225y are suspended from either side of the tip portion of the guide frame 22x on its front surface and have wheels 221y, 221y rotatably fitted into the lower end portions of legs 225y with their axles directed in the Y-axis direction. The lower end of the outer circumference of these wheels 221y is set on the same level as a plane of the guide frame 22x and is brought into contact with the testpiece 3. Accordingly, the wheel legs and the wheels bear the weight of the guide frame 22y and those of other members such as the probe 1b fitted to the guide frame 22y at the front portion of the guide frame 22y.

The motor case 23 is mounted onto the upper portion of the rear surface of the guide frame 22y at its end portion and incorporates the two pulse motors 23x and 23y therein. The pulse motor 23x is positioned above the elongated groove 224x and its axle passes through the slide leg 228y and hangs down into the elongated groove 224x. A pinion 222y is fitted onto the lowermost end of this axle and engages rack 222x. In other words, the pinion 222y is caused to rotate due to intermittent revolution of the pulse motor 23x, and to roll while engaging with the rack 222x, thereby moving the guide frame 22y intermittenty in the X-axis direction.

The pulse motor 23y is positioned further to the rear than the pulse motor 23x and its axle is directed downward. A pulley 223y is secured to the lowermost end of this axle. This pulley 223y is positioned considerably above the bottom wall of the guide frame 22y which has a substantially elongated box shape. Another pulley 227y is rotatably mounted in the tip portion of the guide frame 22y opposite the above mentioned pulley 223y. An endless belt 225y is stretched between these pulleys 223y and 227y, and a slide block 226y is connected to a suitable point on this endless belt 225y. A guide hole (not shown) is bored in the bottom wall of the guide frame 22y extending in the Y-axis direction from the front side of the slide leg to a position near the pulley 223y, and the slide block 226y engages this guide hole and is allowed to freely slide in the Y-axis direction. Due to this construction, when the pulse motor 23y turns intermittently, the belt 225y between both pulleys 223y and 227y rotates so that the slide block 226y is pulled by the belt 225y and intermittently moves in the Y-axis direction.

Figures 4, 5:
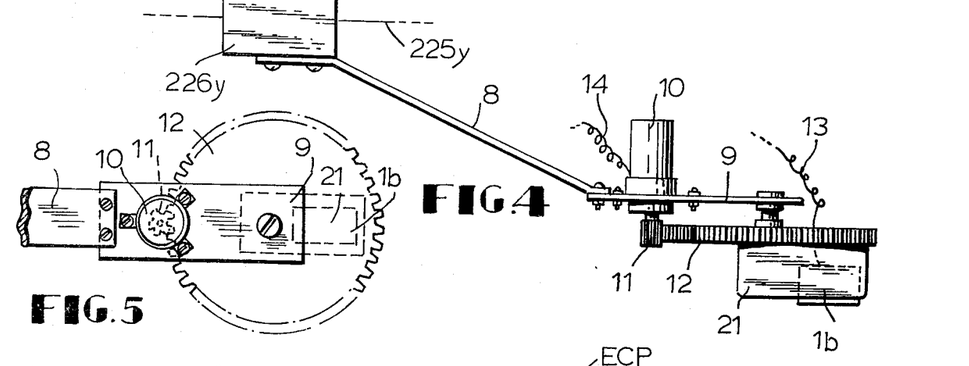
FIG. 4 is a plan view of the portions of the apparatus near the probe.
FIG. 5 is a side view of the portions of the apparatus near the probe.

As shown in FIGS. 4 and 5, a leaf spring 8 is secured onto the lower face of slide block 226y extending downward on the side of the pulley 227y, and a plate-like bracket 9 is secured onto the lower face of slide block 226y extending downward on the side of the pulley 227y, and a plate-like bracket 9 is secured onto the tip portion of the leaf spring 8. A small motor 10 with its axle directed downward and the axle of a large gear 12 which engages a small gear 11 attached to the axle of the small motor 10 are attached to this bracket 9. A holder 21 is attached to the lower face of this large gear 12.

The holder 21 is a rectangular casing having a hollow therein for storing the probe 1b and having a hole for receiving lead wires 13 from the probe 1b to the outside. The direction of the oscillation element (not shown) of the probe 1b is adjusted to carry out angle beam flow detection. The probe 1b is mounted on the holder 21 in such a manner that the ultrasonic wave transmission is directed in the longitudinal direction of the holder 21 and bottom of the probe 1b slightly protrudes beyond the lower surface of the holder 21. Both ends of the lower surface of the holder in its longitudinal direction are rounded as shown in FIG. 4. The curvature of these rounded surfaces is determined by the height of the reinforcement of the weld in the weld zone 3a. The motor 10 is under the drive control of the computer 4 and its lead wire 14 and lead wire 13 of the probe 1b are led to the motor case 23 so that the transmission and reception of signals and the feeding of the drive current are through the cable 7. When the computer 4 generates a predetermined drive signal and applies it to the motor 10, the motor 10 is caused to rotate in the normal or reverse direction until the large gear 12 and hence, the probe 1b, is turned 180 degrees.

Next, an explanation will be given of the signal processing unit.

The main assembly 1a of the ultrasonic flaw detector intermittently generates a high frequency signal to the probe 1b whereby the latter generates an ultrasonic wave and directs it to the testpiece as an incident wave. If any flaw is present in this instance, the probe 1b receives the reflected wave from the flaw, converts it into an electric signal and feeds it back to the main assembly 1a of the ultrasonic flaw detector. The ultrasonic flaw detector main assembly 1a amplifies the signal of the reflected wave and displays it together with a signal generated as an echo pulse for ultrasonic oscillation, that is, the incident pulse, on a cathode ray tube (CRT) incorporated in the unit 1. On the other hand, the ultrasonic flaw detector main assembly 1a receives a gate following signal (GFS) from the computer 4 and in turn transmits a flaw detection data (FDD) in the binary-coded decimal form to the computer 4. The flaw detection data FDD is expressed by first dividing the weld zone 3a into a suitable number of segments (e.g., ten segments) in the Y-axis direction and expressing the level of the echo pulse from each segment in terms of a percentage with the maximum possible echo pulse level being 100%. If, for example, the echo pulse level is represented by a single decimal digit resolution is 10%. The gate following signal GFS is a control signal which causes a gate signal to be generated in an internal circuit inside the main assembly 1a of the ultrasonic flaw detector to follow and change in order to discriminate from which segment, out of the abovementioned ten divided segments, the echo pulse is obtained.

Figure 6:
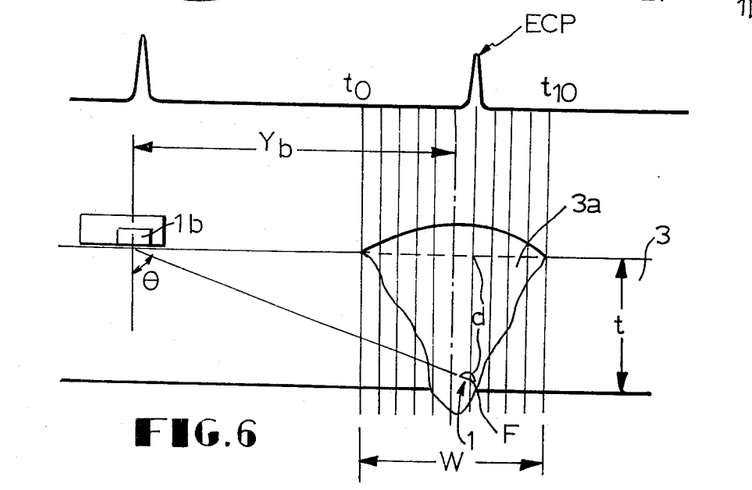
FIG. 6 is a schematic view explaining the gate signal.

FIG. 6 diagrammatically illustrates the relationship between the segments of the weld zone 3a and the flaw detection signal displayed on the CRT of the ultrasonic flaw detector main assembly 1a, wherein it is assumed that the position at one edge of the weld zone 3a on the probe side corresponds to the position $t_0$ on the time axis of the flaw detection signal and the other edge of the weld zone 3a corresponds to the positions $t_{10}$ of the time axis. In other words, the ultrasonic flaw detector main assembly 1a is so constructed that it generates ten gate signals that divide the time axis into ten equal parts within the range of $t_0$–$t_{10}$, and determines the position of the echo pulse ECP on the time axis, that is to say, the position of the flaw F in the segments of the weld zone 3a. Since the gap between the probe 1b and the weld zone 3a varies in accordance with the movement of the probe 1b in the Y-axis direction, it is also necessary to vary the gate signals in accordance with the varying gap. For this purpose, the scanner 2 applies data representing the position of the probe 1b on a set of X-Y ordinates having a suitably selected reference point as an input to the computer 4 as will be described elsewhere. On the basis of this data representing the gap between the given position of the weld zone 3a and the set position of the probe 1b at the start of flaw detection as well as data on the dimension of the weld zone 3a in the X-axis direction (the direction of width), computer 4 calculates and generates the gate following signal GFS to generate gate signals in accordance with the given situation.

As already described, the computer 4 generates the drive signal DVx to the pulse motor 23x and drive signal DVy to the pulse motor 23y and thus controls their revolution. Each motor rotates one step per pulse of the drive signal and actuates the scanner 2 having the aforementioned construction, thereby intermittently moving the probe 1b either in the X-axis direction or in the Y-axis direction. The pulse motors 23x and 23y generate signals reporting to computer 4 that their one-step revolution is completed in the form of signals representing the position of the probe 1b on the X-Y coordinates. By means of these signals, the computer 4 is able to correctly determine the position of the probe 1b on the X-Y coordinates. This can easily be realized by placing the set position of the probe 1b at the start of flaw detection a predetermined distance from the weld zone 3a and a predetermined distance from one side edge of the testpiece 3 in the direction of width (in the X-axis direction) thereby setting the center of the X-Y coordinates. If the reliability of the revolving action of the pulse motors 23x and 23y of the scanner 2 is high, the drive signals DVx and DVy per se can be used as signals for determining the position of the probe 1b without necessarily feeding back the position signals of the probe 1b from the pulse motors 23x and 23y to the computer 4.

Figure 7:
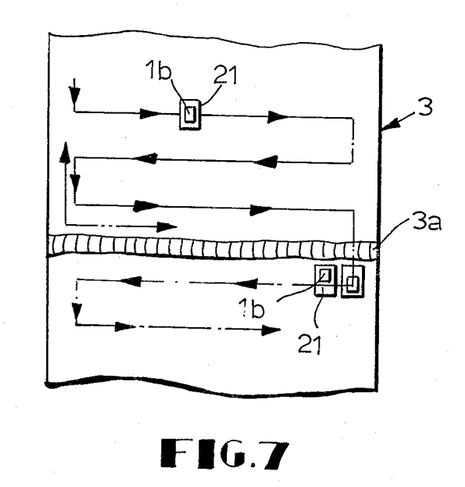
FIGS. 7 and 8 are plan views showing the scanning orbit of the probe.
Figure 8:
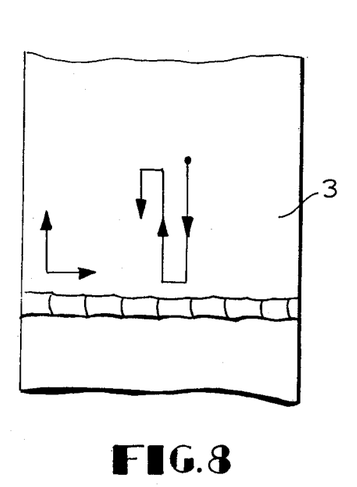

The pattern of motion of the probe 1b by actuation of the pulse motors 23x and 23y, that is, the scanning orbit of the probe 1b, is such that during the initial rough flaw detection the probe 1b moves in the X-axis direction and when the probe 1b reaches the side of the testpiece 3, it moves slightly in the Y-axis direction and thereafter moves again in the X-axis direction, as shown in FIG. 7. During the precision flaw detection made subsequent to the rough flaw detection, the probe 1b moves in the Y-axis direction towards the weld zone 3a and when the probe 1b reaches a position near the weld zone 3a, it then moves in the X-axis direction, and subsequently moves in the Y-axis direction away from the weld zone 3a to a predetermined position on the Y-coordinate and again moves in the X-axis direction, as depicted in FIG. 8.

The computer 4 also generates a drive signal DVr to the small motor 10 so as to turn the probe 1b by 180 degrees. After a series of rough flaw detection scans or precision flaw detection scans is carried out in accordance with the abovementioned pattern, the computer 4 feeds the drive signal DVy to the pulse motor 34y and moves the probe 1b in the Y-axis direction so as to pass over the weld zone 3a. FIG. 7 illustrates the orbit of the probe 1b for the case in which no flaw is detected during the rough flaw detection and hence, no flaw detection is made on one side of the weld zone 3a. When the computer 4 recognizes by means of the probe position signals from the pulse motor 23y that the probe 1b as passed over the weld zone 3a and reaches a predetermined position on the other side of the weld zone 3a, it generates the abovementioned drive signal DVr to turn the probe 1b horizontally by 180 degrees. This enables flaw detection to be made from the other side of the weld zone 3a. Thereafter, the computer 4 feeds the drive signals DVx and DVy to the pulse motors 23x and 23y, respectively, and the probe 1b scans the other side of the weld zone 3a in the same way as described above.

Though not specifically illustrated, suitable interfaces are naturally interposed between the pulse motors 23x and 23y and the motor 10 and between the motor 10 and the ultrasonic flaw detector main assembly 1a.

A printer 5, a plotter 6, a CRT display 50 and a magnetic cassette tape recorder 60 are connected to computer 4 as output devices. The magnetic cassette tape recorder 60 is used for recording flaw detection data initially stored in a buffer memory inside computer 4 after a series of flaw detection scans, and this stored data is reproduced and returned to the buffer memory of computer 4, whenever necessary. After predetermined processing by computer 4, the flaw detection results are displayed on the CRT display 50 and typed out by the printer 5 and the plotter 6.

Figure 9:
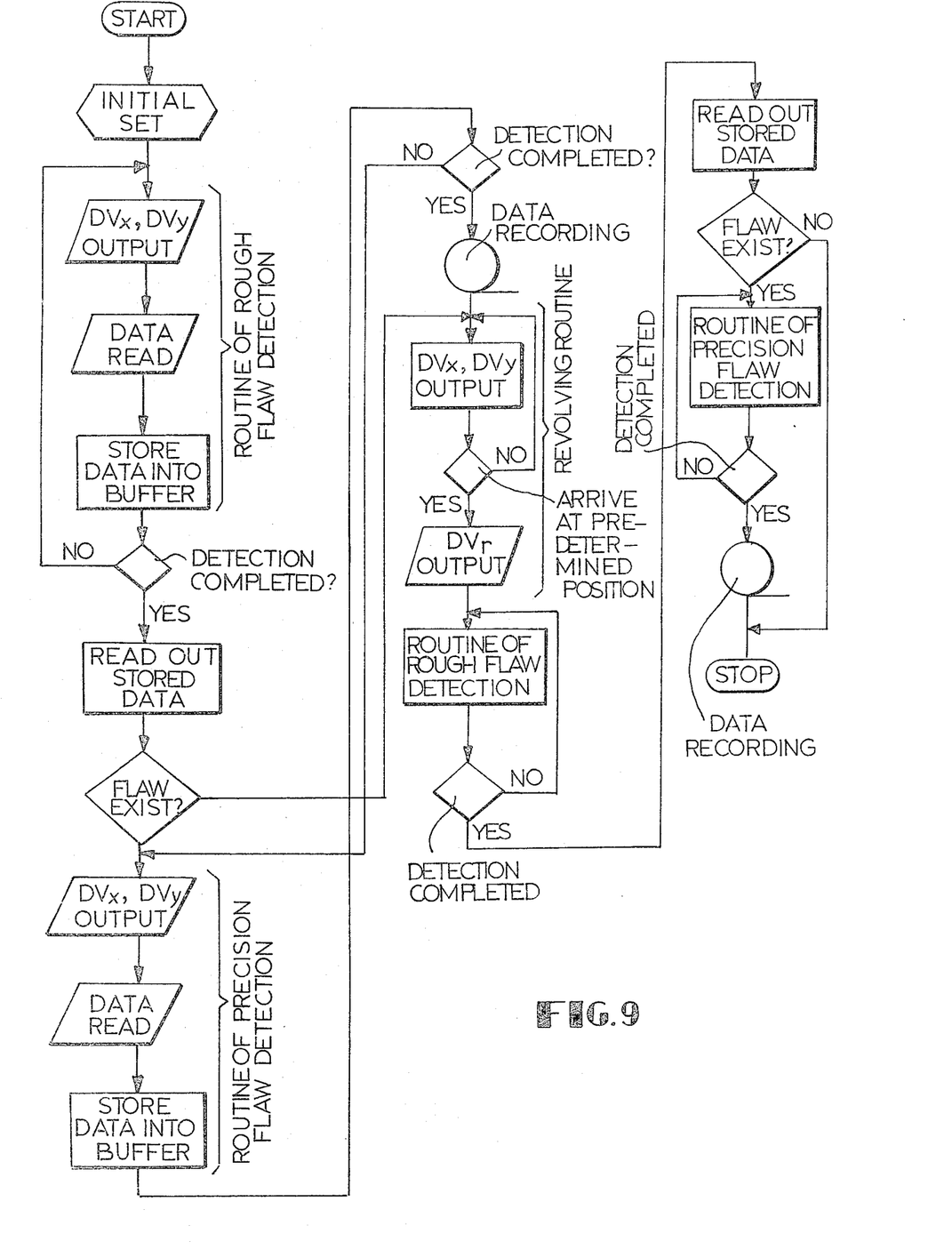
FIGS. 9 and 10 are diagrammatic flow charts explaining the flaw detecting action.
Figure 10:
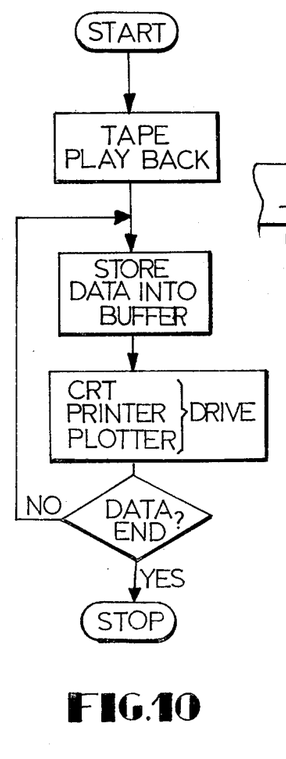

The flaw detecting action of the apparatus of the present invention having the above-described construction will now be explained with reference to the flow-charts illustrated in FIGS. 9 and 10. The flaw detection mechanism is first placed on the testpiece 3 and positioned so that the weld zone 3a is parallel to the guide frame 22x with a predetermined gap between them and is perpendicular to the guide frame 22y. Next, the flaw detection mechanism is secured to the testpiece 3 by fastening the clamp screws 223x. When the signal processing unit is subsequently actuated, the computer 4 is placed in an initial state and it then generates the drive signal DVx for actuating pulse motor 23x and the drive signal DVx for actuating pulse motor 23y so as to transfer the probe 1b to a predetermined position, for example, to the position which is regarded as the center of the X-Y coordinates, in accordance with the given conditions.

When a predetermined key of the computer 4 is subsequently pushed, computer 4 begins a routine of rough flaw detection and generates drive signals DVx and DVy in a predetermined sequence to actuate respective pulse motors 23x and 23y to move guide frame 22y in the X-axis direction along the guide frame 22x and to move slide block 226y in the Y-axis direction along the guide frame 22y. As a result, the probe 1b moves so as to describe the orbit shown in FIG. 7. On the other hand, the ultrasonic flaw detector main assembly 1a generates intermittent high frequency waves so that probe 1b generates ultrasonic waves and thus performs flaw detection with respect to the weld zone 3a. By means of the gate following signals GFS generated by the computer 4 and applied to the ultrasonic flaw detector main assembly 1a, the latter generates output data on the level of the flaw detection signal for each segment and applies this flaw detection data to the computer 4. The computer 4 stores the flaw detection data together with a signal from the scanner 2 representing the position of the probe 1b on the X-Y coordinates in buffers included therein.

Figure 11:
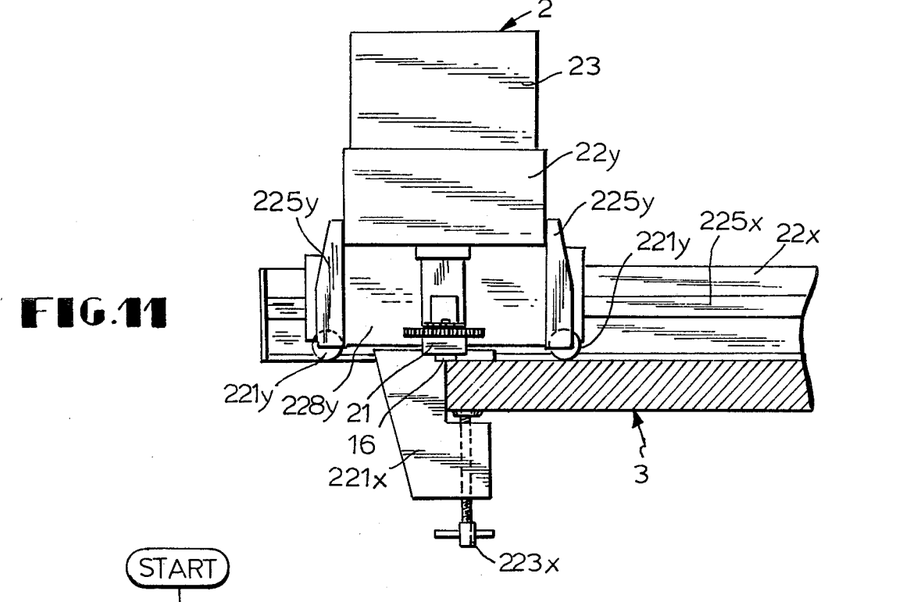
FIG. 11 is a schematic front view showing the scanner when the probe is positioned by the side of the test object.

As to the specific movement of the guide frame 22y for moving the probe 1b in the X-axis direction during the abovementioned flaw detecting action, the slide leg 228y which moves integrally with the guide frame 22y move stably in the X-axis direction because its protuberances 224y engage the recessed grooves 225x of the guide frame 22x. Moreover, the guide frame 22y can move until one of the wheels 221y comes off the side edge of the testpiece 3 and floats in midair as shown in FIG. 11. Due to the engagement between the protuberances 224y and the mating recessed grooves 225x, the guide frame 22y and the pulse motors 23x and 23y mounted thereon are horizontally supported and do not roll or incline with respect to the guide frame 22x so that return movement in the X-axis direction can be made without any trouble. In the apparatus of the present invention, therefore, the probe 1b is placed in a position which substantially coincides with the center line of the guide frame 22y and can be moved over the entire width of the testpiece 3 and hence, flaw detection can be made over the entire width of the weld zone 3a.

During progress of the flaw detection scanning, the computer 4 stores the flaw detection data in its buffer memory. When computer 4 recognizes that the probe 1b has reached a suitable position adjacent to the weld zone 3a it determines that rough flaw detection on one side of the weld zone 3a by probe 1b is completed and cuts off the data transmission to the ultrasonic flaw detector main assembly 1a and to pulse motors 23x and 23y. The computer 4 then reads out the data in the buffer and checks to determine if any flaw is present. If no flaw is present, the computer 4 begins a routine for making rough flaw detection on the other side of the weld zone 3a. In other words, it transmits drive signal DVy to the pulse motor 23y to move probe 1b in the Y-axis direction and ride over the weld zone 3a until it reaches the other side of the weld zone 3a as shown in FIG. 7. Next, the computer 4 generates suitable drive signals DVx and DVy and extinguishes them when the probe 1b arrives at a predetermined position. In this case, it is optional to let computer 4 recognize the predetermined position of the probe 1b as the center of the X-Y coordinates inherent to the other side of the weld zone 3a or to continue to recognize the center of the X-Y coordinates on side of the weld zone where flaw detection has already been completed. Next, computer 4 generates drive signal DVr so as to turn small motor 10 by 180 degrees. This enables flaw detection scanning from one side to the other side of the weld zone 3a. Thereafter, the computer begins the rough flaw detection routine in a manner similar to that already explained. Incidentally, both side edges of the lower face of the holder 21 in the longitudinal direction, to which the probe 1b is fitted, are rounded and the holder 21 is supported by the leaf spring 8 as already described. Accordingly, even when the weld zone 3a rises up considerably, the probe 1b can ride over the weld zone 3a without difficulty.

On the other hand, when any flaw is found on one side of the weld zone 3a as a result of the rough flaw detection, computer 4 begins the precision flaw detection routine. In this precision flaw detection routine, the computer 4 returns the probe 1b to the X-Y coordinates where the flaw was first detected, by referring to data read out from the buffer memory and generates drive signals DVx and DVy in a predetermined sequence so that the probe 1b moves so as to describe the orbit such as shown in FIG. 8 with those X-Y coordinates as the starting point. Incidentally, the pitch of motion of the probe 1b in this instance is finer than that in the rough flaw detection routine, and is about 1–2 mm. While the probe 1b is being moved in this manner, computer 4 reads in the flaw detection data from the main assembly 1a of the ultrasonic flaw detector and also the probe position data from the scanner 2 and stores them in its buffer memory in the same way as in the rough flaw detection routine.

When the rough and precision flaw detection routines are completed for one flaw, the computer 4 begins the precision flaw detection routine for the flaw detected next in order during the rough flaw detection routine as above. After precision flaw detection is completed for all flaws that were detected during the rough flaw detection, computer 4 assumes that flaw detection on one side of the weld zone 3a is completed, and then records the data stored in the buffer memory representative of the flaw detection onto a magnetic recording tape loaded in magnetic tape recorder 60. Thereafter, computer 4 begins the routine of rough flaw detection on the other side of the weld zone 3a after a routine similar to that already mentioned. This rough flaw detection routine is the same as the aforementioned rough flaw detection routine and the precision flaw detection routine subsequent thereto also is the same as that already mentioned. In this case, too, the data in the buffer memory is recorded onto the magnetic tape.

After the series of flaw detection routines are completed in the abovementioned manner, the magnetic tape recorder 60 is placed in the play-back mode so that the flaw detection data recorded on the magnetic recording tape is read into the buffer memory of computer 4, and the results of the flaw detection are displayed by means of the CRT display 50, the printer 5 and the plotter 6. The operational processing for this display may be performed by computer 4. If a computer is also incorporated within the output device itself such as the printer 5, the operational processing may of course be performed by that computer.

The most primitive display format of the printer 5 or the CRT display 50 is such that the flaw detection data from the main assembly 1a of the ultrasonic flaw detector is displayed in the following manner, for example;

418☐25.0☐0002620000

The numerals of the first three digits represents the X-axis coordinate of the probe 1b and the numerals of the second three digits represent the Y-axis coordinates of the probe 1b. Each numeral of the last ten digits represents the level of the echo pulse at each of the ten segments in terms of 10% of the maximum possible echo pulse level as mentioned already. The display illustrated above indicates that the levels of the echo pulses of the fourth, fifth and sixth segments of the weld zone 3a from the axis of the probe 1b are 20%, 60% and 20%, respectively, and more strictly speaking, from 20 to 29%, from 60-69% and from 20 to 29%, respectively, It is also possible by performing the necessary operational processing to display the flaw number, the position of the probe 1b, the level display of the maximum echo pulse, the length and depth of the flaw, the results of grade classification of the flaw (or to display whether or not the flaw is acceptable), and so forth.

Since the level display of the maximum echo pulse, the length of the flaw, etc., can be determined substantially directly from the level of the echo pulse at each segment explanation is hereby omitted. The flaw depth can be determined by carrying out the following operational processing. The horizontal distance from the probe 1b to the flaw F can be expressed by;

$$Y_b - W/2 + N \cdot W/10$$

where:
$Y_b$ is the distance from the probe 1b to the center of the weld zone 3a in the Y-axis direction;
W is the width of the weld zone 3a (in the Y-axis direction); and
N is the number of the segment where the flaw F is present is presently counted from the probe 1b (see FIG. 6).

Hence, the flaw depth d can be expressed as:

$$d = t - |t - (Y_b - W/2 + N \cdot W/10)/\tan \theta|$$

where:
t is the thickness of the testpiece 3; and
$\theta$ is the incident angle of the ultrasonic wave from the probe 1b.

Figure 12:
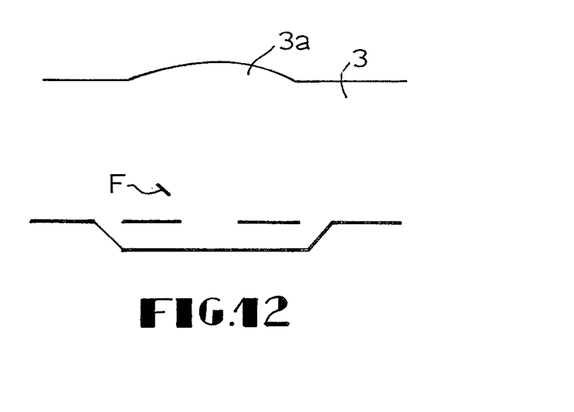
FIGS. 12 and 13 are charts showing the flaw modes.
Figure 13:
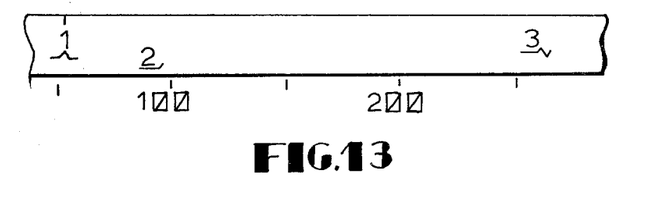

On the other hand, besides the preparation, display and recording of the abovementioned data on the printer 5, the CRT display 50 and the plotter 6 may graphically illustrate the state of the flaws. FIG. 12 illustrates a section of the weld zone 3a as viewed in the X-axis direction and shows the depth of the flaw F in five grades. FIG. 13 is a plan view of the weld zone 3a showing the positions of flaws F together with the flaw numbers obtained by determining the X-axis coordinate of the flaw from the X-axis coordinate data of the probe 1b from the flaw detection data and the Y-axis coordinate from the Y-axis coordinate data and from the number of the segments producing the echo pulses.

The ultrasonic flaw detection apparatus of the present invention has the above-described construction and operates in the above described manner. Hence, the flaw detector is operated by first fixing the flaw detection mechanism such as the scanner 2 at a suitable position on the testpiece using the clamp screws 223x and then operating the necessary switches and the keys to start the flaw detection operation which is carried out automatically. In detecting flaws in the iron skeleton structure of a tall building, for example, the printer 5, the plotter 6 and the CRT display 50 may be removed and the data relating to the weld zones in these high places recorded by the magnetic tape recorder 60 so that the printer 5 and the like may be connected to the computer 4 after completion of the flaw detection at these high places for display of the flaw detection data. Thus, the apparatus is made highly portable. Since the operator of the apparatus has only to attach the flaw detection mechanism, operate the switches, and then remove the flaw detection mechanism, he is able to perform flaw detection at a number of positions quickly and safely.

In the apparatus of the present invention, precision flaw detection is carried out subsequent to any flaw detection during rough flaw detection. For this reason, the apparatus of the invention provides both high flaw detection efficiency and high flaw detection precision. Further, in accordance with the apparatus of the invention the probe is moved bidirectionally, that is, in two directions crossing at right angles with each other, i.e., the X-axis and the Y-axis. Thus the probe is allowed to approach to and depart from a desired position by means of the pulse motors. Accordingly, control of the movement of the probe becomes so simple that recognition of the probe position, and hence, data processing for identifying the flaw position, becomes simple. This enables reduction not only in the size of the hardware of the signal processing unit but also in the software, thereby enhancing the data processing speed.

In the apparatus of the invention, further, flaw detection can be performed from both sides of the weld zone by simply setting the flaw detection mechanism on one side of the weld zone. Hence, it is possible to carry out flaw detection with a high level of accuracy. However, it is of course possible to shorten the time required for the flaw detection by controlling the flaw detection mechanism to detect the flaw from only one side of the weld zone.

Moreover, in the apparatus of the present invention, the guide frame 22y is constantly supported by the guide frame 22x in a stable state due to the engagement between the protuberances 224y and the recessed grooves 225x. Even when one of the wheels 221y comes off the testpiece, therefore, it is possible to keep the probe 1b in reliable contact with the testpiece so that flaw detection can be performed over the entire length of the weld zone, that is to say, over the entire width of the testpiece.

Figure 14:
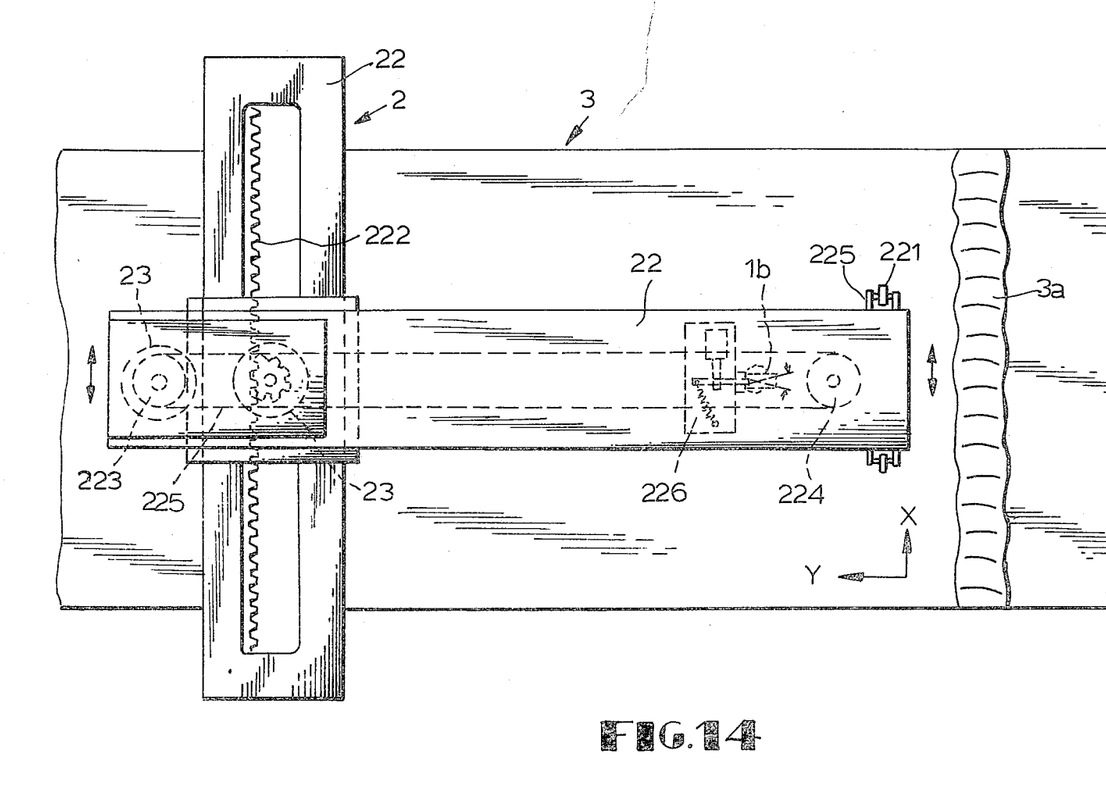
FIG. 14 is a partial plan view of another embodiment of the scanner equipped with an oscillation mechanism.
Figure 15:
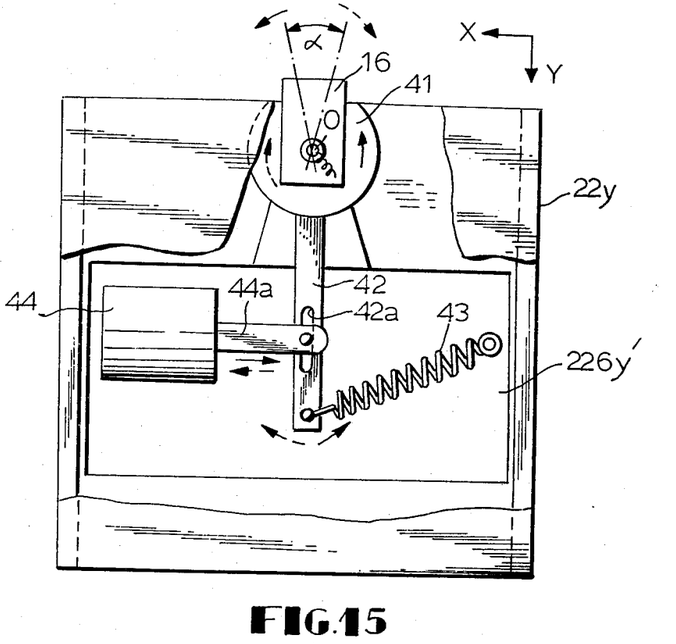
FIG. 15, is a plan view of the oscillation mechanism.

FIG. 14 and 15 illustrate another embodiment of the apparatus of the present invention.

In the apparatus of this embodiment the probe 1b is able to oscillate to the right and left by an angle α with respect to the Y-axis. In the same way as in the previous embodiment, the pulley 223y rotates in an interlocking arrangement with the pulse motor 23y fitted into the guide frame 22y, which is supported by the guide frame 22x and is moved in the X-axis direction by the pulse motor 23x, while the pulley 227y fits into the tip portion of the guide frame 22y so that the slide block 226y' is guided by the guide frame 22y and is moved in the Y-axis direction by the belt 225y stretched between the pulleys 223y and 227y. A rotary member 41 having a column-like shape is embedded in the lower face of the slide block 226' and is allowed to rotate horizontally. The probe 1b is affixed to the lower face of this rotary member 41 and brought into contact with the testpiece 3.

A steering rod 42 is secured to, and extends from, the circumference of the rotary member 41 on the side of the motor case 23. A spring 43 is attached to the tip of the steering rod 42 on the side nearer to the motor case 23 so as to pull the tip to the right as shown in FIG. 15. An elongated hole 42a is formed in the intermediate part of the steering rod 42 between its tip and its base near the side of the rotary member 41 extending in its longitudinal direction. An electromagnetic actuator 44 is disposed on the left of the elongated hole 42 as shown in FIG. 15, so that when its solenoid is excited a rod 44a is drawn into the actuator. The tip of the rod 44a is anchored within the elongated hole 42a. The solenoid of this electromagnetic actuator 44 is fed with an intermittent current and excited by computer 4 (see FIG. 1). Accordingly, the steering rod 42 rotates with the rotary member 41 being its axis. Steering rod 42 is pulled to the left by the rod 44a when the solenoid of the electromagnetic actuator 44 is actuated and it is pulled to the right by the spring 43 when the solenoid is deactuated. As a result, the probe 1b oscillates to the right and the left.

Incidentally, this embodiment does not use the construction in which the probe 1b rides over the weld zone 3a and its direction is changed by 180 degrees. Accordingly, computer 4 controls the electromagnetic actuator 44 instead of the drive control of the aforementioned motor 10. In this case the probe 1b makes one oscillation motion each time the position of the probe 1b is changed by the intermittent revolution of the pulse motors 22x and 23y.

Figure 16:
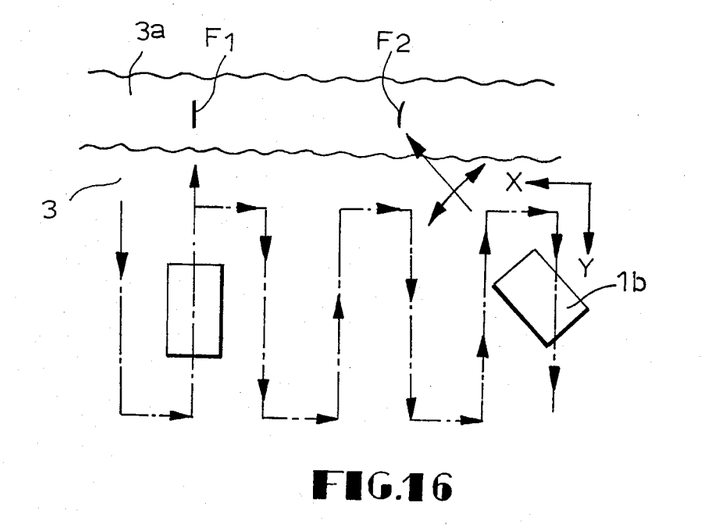
FIG. 16 is a schematic view explaining the action of the scanner equipped with the oscillation mechanism.

In the apparatus having the oscillation mechanism of this embodiment, the ultrasonic waves transmitted by the probe 1b propagate not only in the Y-axis direction but also in directions different from the Y-axis within the angular range α. Accordingly, the apparatus can reliably detect narrow flaws $F_1$ and $F_2$ having shapes extending substantially in parallel to the Y-axis as shown in FIG. 16, without missing them. In order to identify the flaw position(s) from the results of the flaw detection, it is necessary to inform computer 4 of the angle between the Y-axis and the direction of propagation of the ultrasonic waves because the probe 1b oscillates in this embodiment. This can be easily calculated utilizing the timing of the current fed to the electromagnetic actuator 44, and more strictly by providing a rotary encoder in an interlocking arrangement with the rotary member 41 to generate this information.

If the apparatus of this invention is equipped with the abovementioned oscillating mechanism, it can perfectly detect those flaws which have a narrow width and extend substantially in parallel to the Y-axis which would otherwise be missed if the direction of propagation of the ultrasonic waves were fixed in the Y-axis direction only.

As described in detail in the foregoing, the apparatus in accordance with the present invention is easy to operate and performs flaw detection with a high level of accuracy within a short period. Moreover, the apparatus of the invention is compact in size so that it is easy to transport and operate. Thus, the present invention provides a fully automatic ultrasonic flaw detector which is suited for flaw detection even in high places.

We claim:

1. A fully automatic ultrasonic flaw detection apparatus comprising:

a probe for transmitting and receiving ultrasonic waves in a testpiece;

a probe holder having said probe mounted thereon;

a probe scanner connected to said probe holder having a first motor for moving said probe holder back and forth on a first line parallel to the surface of the testpiece and parallel to the area which is to be tested for flaws, and a second motor for moving said probe holder back and forth on a second line perpendicular to said first line and parallel to the surface of the testpiece;

an information processing unit connected to said probe scanner and said ultrasonic transmitting and receiving apparatus having a memory means and a display means (a) for generating drive signals for application to said motors of said probe scanner for moving said probe holder according to a predetermined repeating rough scanning pattern in one direction along a first line, then along a second line for a short distance and then along another first line in the opposite direction, (b) for storing in said memory means flaw detection data indicative of the position of said probe when said probe receives ultrasonic waves from the testpiece and the amplitude of said received ultrasonic waves is indicative of a flaw, (c) for determining the position and characteristics of flaws in the testpiece from said stored flaw detection data, (d) for generating drive signals for application to said motors of said probe scanner for moving said probe holder according to a predetermined repeating fine scanning pattern in the vicinity of the position of each flaw if any flaw position is determined, said pattern being in one direction along a second line, then along a first line for a short distance and then along another second line in the opposite direction; and (e) for displaying the position and characteristics of each such determined flaw on said display means.

2. A fully automatic ultrasonic flaw detection apparatus as claimed in claim 1 wherein said probe scanner further comprises:

a probe holder turning means connected to said probe holder for turning said probe holder in said plane; and a resilient support means connected to said probe holder for resiliently supporting said probe holder in response to any unevenness of the surface of the testpiece.

3. A fully automatic ultrasonic flaw detection apparatus as claimed in claim 2 wherein said information processing unit further comprises means for generating drive signals to said probe holder turning means for turning said probe holder.

4. A fully automatic ultrasonic flaw detection apparatus as claimed in claim 2 or 3 wherein the face of said probe holder disposed nearest to the testpiece has curved edge portions for reducing friction with any raised portions of the testpiece.

5. A fully automatic ultrasonic flaw detection apparatus as claimed in claim 1 wherein said probe scanner comprises a first guide means connected to said probe holder for guiding motion of said probe holder back and forth in a first direction parallel to the testpiece and a second guide means connected to said first guide means for supporting said first guide means for guiding motion of said first guide means in a second direction perpendicular to said first direction and parallel to the testpiece.

6. A fully automatic ultrasonic flaw detection apparatus as claimed in claim 1 wherein said connection between said probe holder and said probe scanner comprises an oscillation mechanism for oscillating the facing of said probe with a plane parallel to a surface of the testpiece.

7. A fully automatic ultrasonic flaw detection apparatus as claimed in claim 6 wherein said oscillation mechanism comprises a spring connected to said probe holder for forcing said probe holder toward a first extreme probe facing and an electromagnetic actuator selectively actuable for forcing said probe holder toward a second extreme probe facing opposite to said first extreme probe facing.

8. A fully automatic ultrasonic flaw detection apparatus as claimed in claim 7 wherein said information processing unit is further connected to said oscillation mechanism for selectively actuating said electromagnetic actuator.

* * * * *